(12) United States Patent
Hueros Soto et al.

(10) Patent No.: US 9,637,755 B2
(45) Date of Patent: May 2, 2017

(54) METHOD FOR PLANT IMPROVEMENT USING A TRANSGENE CONTAINING THE BETL9 PROMOTER DRIVING EXPRESSION OF THE MRP1 PROTEIN

(71) Applicant: Biogemma, Paris (FR)

(72) Inventors: Gregorio Hueros Soto, Meco Madrid (ES); Wyatt Paul, Chappes (FR); Pascual Perez, Chanonat (FR)

(73) Assignee: BIOGEMMA, Paris (FR)

( * ) Notice: Subject to any disclaimer, the term of this patent is extended or adjusted under 35 U.S.C. 154(b) by 0 days.

(21) Appl. No.: 14/437,426

(22) PCT Filed: Oct. 22, 2013

(86) PCT No.: PCT/EP2013/072017
§ 371 (c)(1),
(2) Date: Apr. 21, 2015

(87) PCT Pub. No.: WO2014/064071
PCT Pub. Date: May 1, 2014

(65) Prior Publication Data
US 2015/0291973 A1    Oct. 15, 2015

(30) Foreign Application Priority Data
Oct. 22, 2012    (EP) .................................... 12306306

(51) Int. Cl.
*C12N 15/82*    (2006.01)
*C07K 14/415*    (2006.01)
*A01G 1/00*    (2006.01)

(52) U.S. Cl.
CPC ......... *C12N 15/8261* (2013.01); *A01G 1/001* (2013.01); *C07K 14/415* (2013.01); *C12N 15/8234* (2013.01)

(58) Field of Classification Search
None
See application file for complete search history.

(56) References Cited

FOREIGN PATENT DOCUMENTS

| EP | 1 528 104 A1 | 5/2005 |
| WO | WO-2007/093623 A1 | 8/2007 |
| WO | WO 2007/093623 A1 * | 8/2007 |

OTHER PUBLICATIONS

Gómez et al., 2002, The Plant Cell 14: 599-610.*
One repeat myb transcriptional factor from *Zea mays*, Gen Bank accession No. CAC86578.1, published Apr. 4, 2002.*
çakir, 2004, Fields Crop Research 89: 1-16.*
Gomez, E. et al., "Establishment of cereal endosperm expression domains: Identification and properties of a maize transfer cell-specific transcription factor, ZmMRP-1." *The Plant Cell* 14(3): 599-610 (2002).

* cited by examiner

*Primary Examiner* — Amjad Abraham
*Assistant Examiner* — Bratislav Stankovic
(74) *Attorney, Agent, or Firm* — Polsinelli PC (57) ABSTRACT

The invention relates to the field of plant improvement, in particular of the improvement of yield for plants, by using a transgene containing the BETL9 promoter driving expression of the MRP1 protein.

3 Claims, 3 Drawing Sheets

| Events [Zmbet9/MRP1] | 2010 Heat stress | | | 2010 Normal condition | | | 2011 Heat stress | | | 2011 Normal condition | | |
|---|---|---|---|---|---|---|---|---|---|---|---|---|
| | Yield (Qx/ha) | % yield of control | p-value | Yield (Qx/ha) | % yield of control | p-value | Yield (Qx/ha) | % yield of control | p-value | Yield (Qx/ha) | % yield of control | p-value |
| FUS5.10 | 31,4 | 128 | 0,0027 | 50,6 | 100 | 0,9464 | 35,1 | 100 | 0,9488 | 58,2 | 104 | 0,3954 |
| FUS5.12 | 31,1 | 127 | 0,0042 | 51,4 | 101 | 0,8600 | 37,3 | 106 | 0,3058 | 54,8 | 98 | 0,6492 |
| FUS5.1b | 29,3 | 119 | 0,0340 | 49,4 | 97 | 0,6644 | 30,9 | 88 | 0,0469 | 47,2 | 84 | 1,0E-03 |
| FUS5.3a | | | | | | | 39,6 | 113 | 0,0382 | 59,0 | 105 | 0,2604 |
| Control NB1 | 24,5 | 100 | NA | 50,8 | 100 | NA | 35 | 100 | NA | 56 | 100 | NA |

Figure 3

METHOD FOR PLANT IMPROVEMENT USING A TRANSGENE CONTAINING THE BETL9 PROMOTER DRIVING EXPRESSION OF THE MRP1 PROTEIN

RELATED APPLICATIONS

This application is a national stage application (under 35 U.S.C. §371) of PCT/EP2013/072017, filed Oct. 22, 2013, which claims benefit of European application EP12306306.7, filed Oct. 22, 2012.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 15351_27_US_Sequence_Listing. The size of the text file is 6 KB, and the text file was created on Apr. 21, 2015.

The invention relates to the field of plant improvement, in particular of the improvement of yield for plants.

Cereals are grasses (members of the monocot family Poaceae, also known as Gramineae) cultivated for the edible components of their grain, composed of the endosperm, germ and bran.

In the context of the present invention a cereal shall mean in particular maize, rice, wheat, barley, sorghum, millet, oats, rye, triticale (hybrid of wheat and rye), fonio, as well as two pseudocereals, namely buckwheat and quinoa.

Maize and wheat are the preferred cereals according to the invention.

In agriculture, yield is the amount of product harvested from a given acreage (eg weight of seeds per unit area). It is often expressed in metric quintals (1 q=100 kg) per hectare in the case of cereals. It is becoming increasingly important to improve the yield of seed crops to feed an expanding population and, more recently, for biofuel production. One strategy to increase the yield is to increase the seed size, provided that there is not a concomitant decrease in seed number.

Some authors have described plants which present larger grains than control plants.

In particular, WO 2005/085453 deals, in its introduction, with the problem of increasing yield through increase of the seed size.

This patent application reviews different strategies in order to increase seed size, and cites some patent applications related to genes that are supposed to be of interest for increasing seed size. This patent application describes a mutant obtained in *Arabidopsis thaliana*, which presents larger seeds than controls.

This application speculates on the possibility to inhibit the gene mnt (as described), which is actually the arf2 gene (for auxin response factor 2) in various plants in order to increase seed size.

The data shown in this document indicates that presence of larger seeds is no necessarily linked to increase in yield, although this may present some interest for some applications, such as starch or oil processing.

The MRP1 protein has been described in Gomez et al (Plant Cell, 14, 599-610, 2002). The authors proposed a role in the transfer cells differentiation.

Gomez et al (Plant Cell, 21, 2022-2035, 2009) describes transgenic maize plant comprising the gene encoding for MRP-1 protein expressed under the promoter AL-9, a promoter specifically active in the aleurone layer. This was the first success of transgenic plant expressing ectopically MRP-1. The author showed that the expression of MRP-1 induced the development of an ectopic endosperm transfer layer in the aleurone area. The author concluded to a possible MRP-1 function in the cell to cell communication and signaling.

Besides this characteristic in the kernel development, the plant did not show any other phenotypes.

US20100306876 reports that early overexpression of the transactivator MRP1 in the BETL leads to seeds with a hypertrophied BETL layer. Since the BETL layer is important for nutrient flow into the developing endosperm, this hypertropy leads to the production of a larger endosperm and a larger seed. However in some genetic backgrounds or crops this hypertrophy gives a larger endosperm at the expense of embryo development. Thus although the resulting seed has a higher endosperm to embryo ratio and thus a higher value, the MPRP1 transgene can not be used due to poor seed germination.

The invention provides a transgene that makes it possible to obtain transgenic plants that have an increased yield with regards to isogenic plants that do not contain said transgene.

As intended herein, two plants are said to be "isogenic" when they differ at very few loci (less than 20, more preferably less than 10), and when one does carry the transgene, while the other does not. These plants can also be called "virtually isogenic".

According to the invention, said transgene comprises an expression cassette comprising a nucleic acid molecule comprising the BETL9 promoter represented by SEQ ID N° 1, operatively linked to a nucleic acid coding for the MRP1 protein represented by SEQ ID N° 2.

The BETL9 promoter is also described as sequence 18 from US20090307795, sequence 32 from US20080313778 and sequence 69 from US20120011621.

The nucleic acid sequence and amino acid sequence of the MRP1 protein of maize (ZmMRP1) are also shown in SEQ ID N° 51 and 52, respectively of US20100306876.

The invention also encompasses a vector containing the expression cassette of the invention.

A vector, such as a plasmid, can thus be used for transforming host cells. The construction of vectors for transformation of host cells is within the capability of one skilled in the art following standard techniques.

The decision as to whether to use a vector for transforming a cell, or which vector to use, is guided by the method of transformation selected, and by the host cell selected.

Where a naked nucleic acid introduction method is used, then the vector can be the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, K B (1987), Methods in Enzymology).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

For transformation methods within a plant cell, one can cite methods of direct transfer of genes such as direct micro-injection into plant embryos, vacuum infiltration or electroporation, direct precipitation by means of PEG or the bombardment by gun of particules covered with the plasmidic DNA of interest.

It is preferred to transform the plant cell with a bacterial strain, in particular *Agrobacterium*, in particular *Agrobacterium tumefaciens*. In particular, it is possible to use the method described by Ishida et al. (Nature Biotechnology, 14, 745-750, 1996) for the transformation of Monocotyledons.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

For transforming bacteria, a vector is generally defined as being a nucleic acid molecule that possesses elements that allows it to be maintained within said host cell (such as an origin of replication that works in this bacterial host cell).

The invention also encompasses a host cell containing the expression cassette as described above.

The decision as to whether to use a given host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably an Angiosperm plant cell, Monocotyledon as Dicotyledon plant cell, particularly a cereal or oily plant cell, selected in particular from the group consisting of maize, wheat, barley, rice, rape and sunflower, preferentially maize.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

In a specific embodiment, said expression cassette is stably integrated within the genome of said host cell. This embodiment is particularly interesting for plant host cells. Stable integration within the genome means that the expression cassette can be transmitted to the progeny of said host cell upon division.

The invention also encompasses a plant containing at least one cell containing the expression cassette as defined above, preferably stably integrated within its genome.

A part of a transgenic plant, in particular fruit, seed, grain or pollen, comprising such a cell or generated from such a cell is also encompassed by the invention.

It is reminded that a whole plant can be regenerated from a single transformed plant cell. Thus, in a further aspect the present invention provides transgenic plants (or parts of them) including the expression cassette according to the invention. The regeneration can proceed by known methods.

The seeds which grow by fertilization from this plant, also contain this transgene in their genome.

Said plant or part of a plant according to the invention can be a plant or a part of it from various species, notably an Angiosperm, Monocotyledons as Dicotyledons.

It is preferably a cereal or oily plant. As used herein, the term "oily plant" denotes a plant that is capable of producing oil, and preferably that is cultivated for oil production.

Said plant is preferably selected from the group consisting of maize, rice, wheat, barley, rape and sunflower. In a preferred embodiment, said plant is maize. In another preferred embodiment, said plant is wheat The invention thus relates in particular to a transgenic maize or a transgenic wheat, containing at least one cell comprising, stably integrated in its genome, the expression cassette of the invention.

In a specific embodiment, said plant, in particular said maize, comprises multiple cells containing, stably integrated in their genome, the expression cassette of the invention. In this embodiment, it is possible that some cells of said plant do not contain the transgene.

Due to the use of the BETL9 promoter, expression of the MRP1 protein is thus predominant in the endosperm, and in particular in the BETL, preferably an exclusive pattern expression in the BETL. This may be observed by performing Northern blot on RNA obtained from different organs of the plant, and detecting an expression at least ten times higher in the endosperm, and in particular in the BETL, than in other organs.

In another embodiment, said transgene (comprising the expression cassette of the invention) is present in all cells of said plant, in particular said maize or wheat.

In another embodiment, the transgene is introduced within the plant cells such as being expressed transiently, or through a genetic construct not integrated in the genome. Thus, agro-infiltration or any other methods, such as injection or spray, are contemplated for transient expression.

Hybrid plants obtained by crossing plants according to the invention also form part of the invention, when they contain at least one cell containing the expression cassette of the invention.

Any plant as described above can contain one or more transgenes in addition to the cassette according to the invention. One may mention transgenes conferring male sterility, male fertility, resistance to a herbicide (notably glyphosate, glufosinate, imidazolinone, sulfonylurea, L-phosphinotricine, triazine, benzonitrile), resistance to insects (notably a transgene coding for a *Bacillus thuringiensis* toxin), tolerance to water stress. These plants can be obtained by crossing said plants of the invention with other plants containing said transgenes. Alternatively, plants can be co-transformed with an expression cassette containing several different transgenes, including the transgene of the invention.

As demonstrated in the examples, said transgenic plants present an increased yield as compared to non-transgenic plants.

Said increased yield may be observed in normal conditions or in stress conditions.

As intended herein, stress conditions comprise specific conditions that are applied to a plant at a specific development stage such as that they induce a yield decrease of at least 10%, preferentially at least 15% and more preferentially at least 20% between the control plants in normal and in stress conditions. As a matter of illustration, one can cite heat stress conditions that may be applied during the flowering stage (in particular for wheat) or hydric stress before the flowering stage or after the fertilization, (in particular during the grain filling stage for maize).

Consequently, the invention also relates to various methods of using the plants of the invention.

Therefore, the invention also relates to a method for obtaining a transgenic plant containing at least one cell comprising a transgene comprising the expression cassette as described above, comprising the steps consisting of:

a) transforming at least a plant cell or plant tissue with a vector according to the invention;

b) cultivating the cell(s) or plant tissue thus transformed so as to generate a plant containing in its genome at least the expression cassette of the invention, whereby said generated plant contains at least one cell which comprises the transgene comprising the expression cassette as described above.

Said generated plant has increased yield as compared to an isogenic plant that does not contain said expression cassette in its genome.

In this method, it is clear that the increase of yield is checked by sowing and harvesting of a multiplicity of plants that contain the transgene, the yield of which is then compared with the yield obtained with a second group of plants not containing said transgene, and this under the same culture conditions (sowing and harvest at the same time, on comparable parcels, use of the same amount of fertilizers, water . . . ).

It is also clear that comparison is to be performed on a second group of plants that is isogenic to the cereals having the transgene. As indicated above, these "isogenic" plants differs from the plants harboring the transgene at very few loci (less than 20, more preferably less than 10), in addition to not carry said transgene. In particular a plant carrying the transgene isogenic to another plant of interest may be obtained by at least four backcrosses in the isogenic plant of interest, followed by at least one self-fertilization. Preferably, the isogenic plants are homozygous lines.

Said generated plant can also be used in a selection (breeding) process for obtaining a plant with improved yield.

The invention thus also relates to a method for producing a plant that can be used in a selection (breeding) process or scheme for obtaining a plant with improved yield, comprising the step of transforming a plant cell with a vector according to the invention, and regenerating a transgenic plant which comprises at least one cell which contain the transgene comprising the expression cassette as described above.

The introgression of the transgene in a given plant is in particular carried out by selection, according to methods known in the art (crossing and self-pollination). The plants are in particular selected using molecular markers.

The principle is recalled below:

A series of back crosses are performed between the elite line (in which one wishes to introduce the determinant) and a line that already carries said determinant (the donor line). During the back crosses, one can select individuals carrying the determinant and having recombined the smallest fragment from the donor line around the determinant. Specifically, by virtue of molecular markers, the individuals having, for the markers closest to the determinant, the genotype of the elite line are selected.

In addition, it is also possible to accelerate the return to the elite parent by virtue of the molecular markers distributed over the entire genome. At each back cross, the individuals having the most fragments derived from the recurrent elite parent will be chosen.

Selection is important as it is often preferable to sow and harvest plant lines that have been optimized, in particular for the location in which they are cultured. Consequently, one needs to introduce the transgene in said adapted lines having otherwise agronomic quality characteristics.

The invention also relates to a method for obtaining a plant containing a transgene, wherein said transgene comprises the expression cassette as described above, comprising the steps of a) Performing the method as described above (transformation of plant cells and regeneration) in order to obtain a transgenic plant, wherein said transgene comprises said expression cassette, b) crossing said transgenic plant with a plant line which does not contain said transgene (the receiver plant line)

c) selecting, among the progeny, plants that contain said transgene and that have a good genome ratio with regard to said receiver plant line, d) back-crossing said selected plants with said receiver plant line e) repeating steps c) and d) if necessary until a line isogenic with said receiving line (and containing said transgene) is obtained, f) optionally, performing self-fertilization in order to obtain a plant homozygotic for the transgene.

The selection of step c) is preferably performed, by genotyping using molecular markers (for example microsatellite markers), making it possible to define the contribution of each of the two parents to the progeny. One would thus select, in the progeny, plants carrying the transgene and having more markers from the receiver plant line than from the parent containing the transgene.

Plants (in particular maize or wheat) which possess the transgene, may also be selected from the progeny, in a conventional manner by molecular biology methods (such as PCR or Southern blotting).

The invention also relates to a method for increasing plant yield for plant harvest, comprising the step of sowing plant seeds, wherein said plant seeds contain the expression cassette of the invention and growing plants from these sowed seeds, and wherein the yield obtained from said grown plants is increased as compared to the yield obtained from isogenic plants grown from seeds which do not contain said expression cassette.

The invention also relates to a method of growing plants, comprising the step of sowing the plants of the invention, and growing plants from the sowed seeds.

The invention may also comprise the step of harvesting said plants.

The invention also relates to a method for harvesting plants comprising the step of harvesting plants of the invention.

A method for selecting a plant that can be used in a selection (breeding) process for obtaining a cereal with improved yield, which comprises the step of selecting, in a population of plants, the plants containing the expression cassette as described above, is also part of the invention.

In a specific embodiment, the selection is performed through the use of a marker that is specific to the transgene. In this embodiment, the selection step is thus preferably preceded by a step comprising genotyping said population of cereals.

In a specific embodiment, the selection step is preceded by a step comprising extracting the RNA from the individuals in said population.

In a specific embodiment, the selection step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the receiver plant line).

A method for identifying a plant with improved yield, which comprises the step of identifying, in a population of plants, the plants containing the expression cassette as described above, is also part of the invention.

In a specific embodiment, the identification is performed through the use of a marker that is specific to the transgene. In this embodiment, the identification step is thus preferably preceded by a step comprising genotyping said population of cereals.

In a specific embodiment, the identification step is preceded by a step comprising extracting the RNA from the individuals in said population.

In a specific embodiment, the identification step is preceded by a step comprising extracting proteins from the individuals in said population.

In a specific embodiment, said population is the progeny obtained from crossing a transgenic plant, wherein said transgene comprises the expression cassette as described above, with a plant line which does not contain said transgene (the receiver plant line).

The invention also relates to a method for obtaining a hybrid plant, wherein said hybrid plant contains the expression cassette as described above stably integrated within its genome. Said method comprises the step of crossing a first homozygous line, which contains said expression cassette stably integrated within its genome, with a second homozygous line.

This plant can be homozygous (if each homozygous parent has the expression cassette as described above stably integrated within its genome) or heterozygous for the transgene present on said expression cassette.

In a preferred embodiment, the methods are applied to a cereal (in particular, rice, maize, wheat, barley). It is preferred when said plant is maize or wheat.

EXAMPLES

Example 1

Cloning of ZmMRP-1 Downstream the BETL9 Promoter and Transformation

The ZmMRP1 coding sequence was amplified from the MRP1 cDNA (Gomez et al 2002) using the primers

```
                                      (SEQ ID No 3)
5' AGGTCGACGGGATCCATGAATCCCAACTTCAACAGTGTGTGG 3'
and (SEQ ID No 4)
5' TCAAGCTTATCGGTTATATATCTGGCTCTCCTCC 3'
``` such that the ZmMRP-1 coding region could be cloned into SalI, HindIII cut pBSKSII (Stratagene). Next ZmMRP-1 was excised from this plasmid as a SalI, PstI fragment and cloned into SalI, PstI-cut pBIOS503 forming the GATEWAY ENTRY clone pBIOS815. (pBIOS503 is a derivative of pENTRD/Topo (Invitrogen) containing a polylinker with the sites Eco47 III-SalI-Sma I-Pst I between the aatL1 and aatL2 recombinase sites.)

Figure 2:
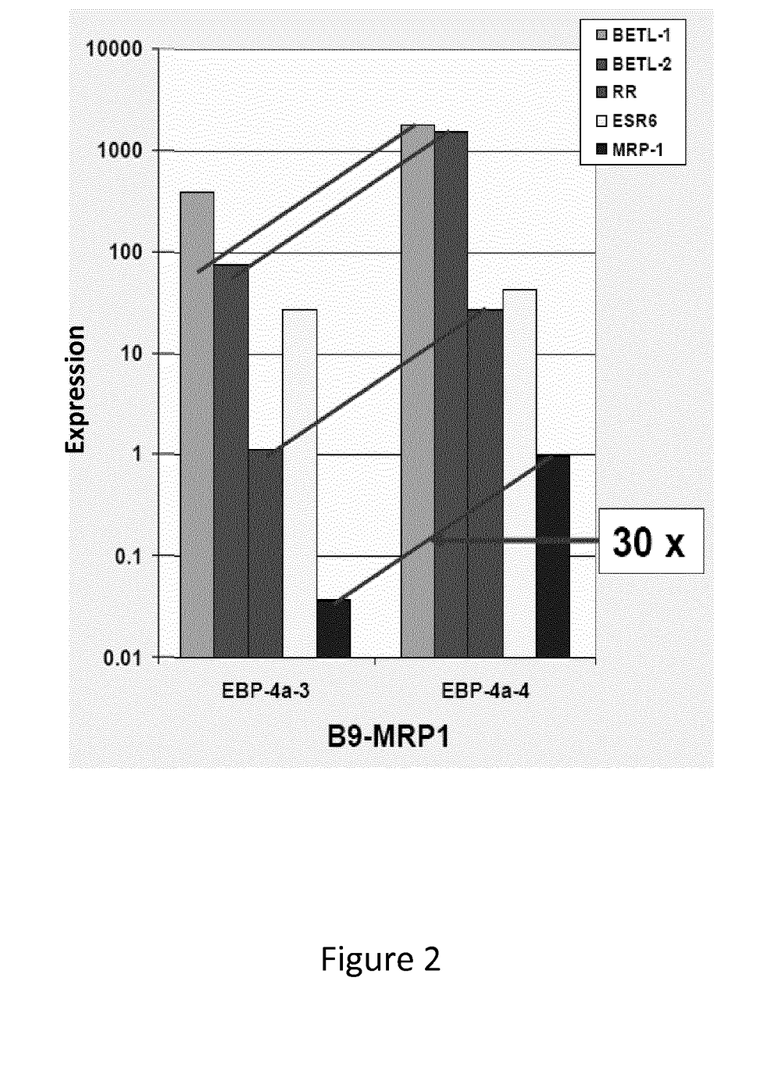
FIG. 2: expression in pBETL9-MRP1, measured by Q-PCR, of ZmMRP-1, BETL1, BETL2, RR and ESR6 transcripts in transgenic (EBP-4a-4) and a non-transgenic, segregant seed (EBP-4a-3).
Figure 3:
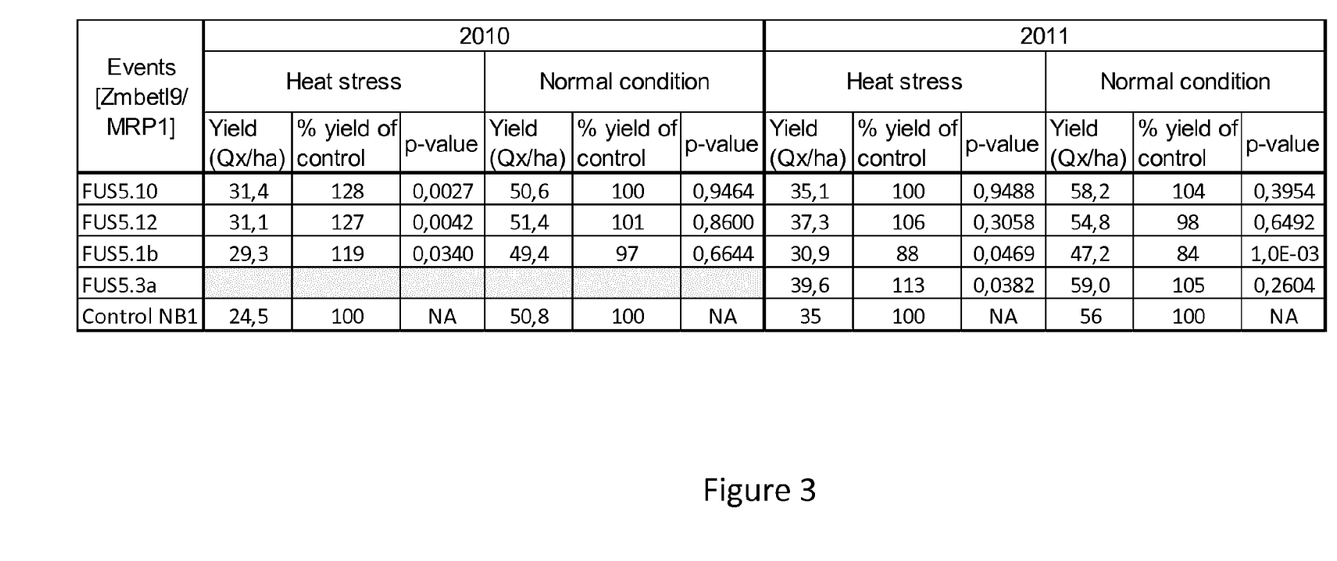
FIG. 3: yield (expressed in Q/ha) for 4 wheat transformants

The BETL9 gene was isolated by Hueros et al (1995). The promoter sequence is, in part, described as pEND1 Patent WO 00/12733. FIG. 2 shows that by Northern and in situ analysis BETL9 is expressed in the lower half of the seed in the BETL. This analysis is confirmed by analysis of pBETL-GUS transgenic maize plants (FIG. 3). BETL9 is expressed early in BETL development, from 4-6 DAP (data not shown).

The 1904 bp maize BETL9 promoter was amplified by PCR from genomic DNA of the inbred line F2 using the primers:

```
pBETL9forXho
                                      (SEQ ID No 5)
5' CCCTCGAGTTACTCATGATGGTCATCTAGG 3',
and pBETL9revXba
                                      (SEQ ID No 6)
5' GCTCTAGAGGGTATAACTTCAACTGTTGACGG 3'.
```

These primers introduce an XhoI and an XbaI site 5' and 3' to the BETL9 promoter.

Figure 1:
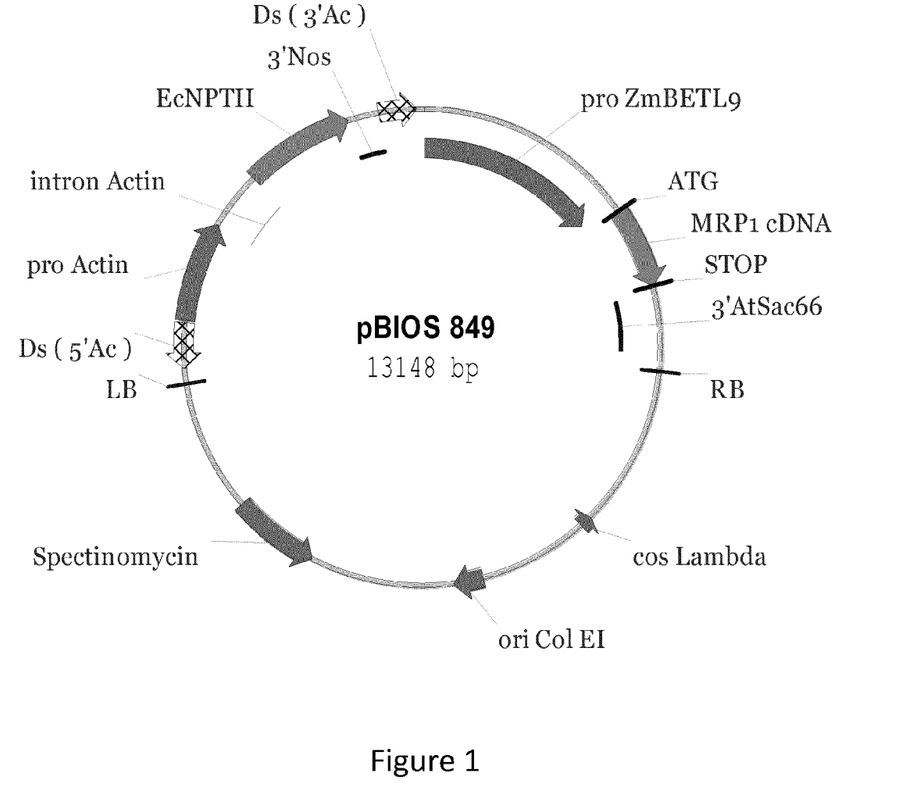
FIG. 1: map of the vector pBIOS849 which is used for expression of ZmMRP-1 in the BETL from the BETL9 promoter.

The PCR fragment was cloned as an XhoI, XbaI fragment into XhoI, XbaI-cut pBSKII forming pBETL9-BS. A GATEWAY cassette and a Sac66 polyadenylation sequence was cloned from pBIOS652 as a HindIII (filled), SacI fragment into XbaI (filled), SacI-cut pBETL9-BS thus forming pBIOS710. An LR clonase reaction was performed between pBIOS815 and pBIOS710 thus forming pBIOS817. The pBETL9-ZmMRP-1-Sac66 polyA chimeric gene from pBIOS817 was cloned as an XhoI fragment into XhoI-cut pBIOS340, forming pBIOS849. (The binary vector pBIOS340 is a derivative of pSB12 (Komari et al. (1996)) containing a pActin+actin intron-NptII nos polyA chimeric gene for selection of maize transformants).

pBIOS849 (FIG. 1) was transferred into agrobacteria LBA4404 (pSB1) according to Komari et al (1996). Maize cultivar A188 was transformed with these agrobacterial strains essentially as described by Ishida et al (1996).

Wheat immature embryos were transformed with the same agrobacterial strains essentially as described by WO 00/63398.

Example 2

Transformed Corn Plant Analysis

Analysis of the pBETL9-MRP1 transformed corn plants indicated that some plants overexpressed ZmMRP-1 (FIG. 2).

Q-PCR analysis showed that transgenic seed expressed 30-fold higher transcript levels of the BETL genes BETL1, BETL2 and TC-RR, whereas expression of ESR6 which is expressed in the Embryo Surrounding Region (ESR) was unchanged in transgenic and non transgenic segregant seed from the same cob (FIG. 2).

Sections of transgenic seed showed an abnormally well-developed BETL that expressed high levels of BETL1 and BETL2 protein (in wild-type seed the BETL1 antibody does not detect the secretion of BETL1 protein from the BETL, but in transgenic seed BETL1 can be seen both in the BETL and in the maternal pedicel region).

These plants possess seeds that are larger than segregant seeds that lack the transgene and thus do not express ZmMRP-1. The transgenic seed of these plants also possess improved pathogen resistance compared to segregant seeds that lack the transgene and thus do not express ZmMRP-1.

Example 3

Transformed Wheat Plant Analysis

Transgenic plants were generated using pBIOS849. Selection of events was based on molecular characterization (simple copy, monolocus).

Example 4

Corn Field Trials

Field trials show that seed yield and the stability of yield are improved.

A—Field Trials

Hybrids with a tester line were obtained from T3 plants issued from the MRP1 transgenic maize line (proBETL9+ZmMRP1+Sac66 term) chosen according to example 2.

The transformants (T0) plant was first crossed with the A188 line thereby producing T1 plants. T1 plants were then self pollinated twice, producing T3 plants which are homozygous lines containing the transgene. These T3 plants were then crossed with the tester line thereby leading to a hybrid. This hybrid is at a T4 level with regards to the transformation step and is heterozygous for the transgene. These hybrid plants are used in field experiments.

Control hybrids are obtained as follows:

Control Equiv corresponds to a cross between a A188 line (the line used for transformation) and the tester line.

Control T 00260 corresponds to a cross between a null segregant (isolated after the second self-pollination of the T1 plants) and the tester line. Said null segregant is a homozygous line which does not bear the transgene. Although the null segregant theoretically presents the same genome as A188, it has undergone in vitro culture (via the steps of callus differentiation and regeneration) and may thus present mutations (either genetic or epigenetic) with regards to a A188 line that has not undergone in vitro culture.

These two control lines are used to avoid any effect that could be due to mutations (genetic or epigenetic) coming from in vitro culture.

Improved yield was observed for the hybrid corn plants containing the MRP1 construct as compared to the controls, as can be seen in Table I. The yield observed ranged from 102% to 111% of the mean of the yield of the controls. No effect on seed moisture content was observed.

Yield was calculated as follows:

During harvest, grain weight and grain moisture are measured using on-board equipment on the combine harvester.

Grain weight is then normalized to moisture at 15%, using the following formula:

Normalized grain weight=measured grain weight×
(100−measured moisture (as a percentage))/85
(which is 100−normalized moisture at 15%).

As an example, if the measured grain moisture is 25%, the normalized grain weight will be: normalized grain weight=measured grain weight×75/85. Yield is then expressed in a conventional unit (such as quintal per hectare).

B—Experimental Design:

Field trials were conducted in 2009 (3 locations) and 2010 (two locations) In 2009, plants were sown between Jun. 15 and Jun. 25, 2009, Harvest was between the 10th and the 12th of November, 2009.

In 2010, plants were sown between the 6th and 18th of May 6. Harvest was between the 15th and 29th September, 2010.

The experimental block comprised of between 5 and 6 replicates. The experimental design was Randomized complete block or Lattice. Each replicate comprised of two row plots with about 62 plants per plot at a density of 73 800 plants/ha.

Two controls were used present in this experiment as described above (a null segregant T00260 and a control equivalent (A188 crossed with the tester line). The Results are represented in Table I, with the yield expressed in (Qx/ha). This table demonstrates that the transgenic plants present an increased yield (normalized for moisture). No other phenotypes were observed for these plants.

TABLE I yield (expressed in Qx/ha) for T 00260-6 tranformant

| Year | Site | Number of replicates | Control Yield (Qx/Ha) | T 00260-6 Yield (Qx/Ha) | % Yield of Control | P value compared with the mean of controls |
|---|---|---|---|---|---|---|
| 2008 | Henderson | 3 | 91.8 | 94.6 | 103 | 0.5027 |
| 2008 | Bluffton | 5 | 65.8 | 63.2 | 96 | 0.5163 |
| 2009 | Huxley | 6 | 78.5 | 80.0 | 102 | 0.4300 |
| 2009 | Arlington | 6 | 77 | 79.2 | 103 | 0.2731 |
| 2009 | Bluffton | 6 | 71.8 | 77.2 | 108 | 0.2244 |
| 2010 | Alleman | 5 | 63.5 | 70.4 | 111 | 0.0204 |
| 2010 | Masson | 5 | 61.9 | 65.9 | 107 | 0.037 |
| 2011 | Finch | 7 | 71.9 | 68.5 | 95 | 0.1769 |
| 2011 | Masson | 7 | 56.5 | 53.4 | 95 | 0.0119 |

Example 5

Wheat Field Trials

Field trials show that stability of yield is improved.

A—Field Trials

Homozygous transgenic lines were selfed for seed increase. T4 (proBETL9+ZmMRP1+Sac66 term) homozygous plants were used for field trial Controls are obtained by bulking null segregant sibling isolated from T1 segregation screened by qPCR. The untransformed line is also included as a separate control. These two control lines are used to avoid any effect that could be due to mutations (genetic or epigenetic) coming from in vitro culture. No significant difference is observed between the two controls and thus the wild type line is used for statistical analysis.

Improved yield was observed for wheat plants containing the MRP1 construct as compared to the controls, as can be seen in FIG. 3. Two conditions were tested: normal conditions and heat stress condition whereby temperatures measures during flowering were equal or above 30° C. for at least five hours out of 24 h during several days in a row.

In normal conditions, the yield observed ranged from 98% to 105% of the mean of the yield of the controls with a global average of 102%. No effect on seed moisture content was observed.

In stressed conditions, the yield observed ranged from 100% to 128% of the mean of the yield of the controls with a global average of 115%. No effect on seed moisture content was observed.

Yield was calculated as follows:

During harvest, grain weight and grain moisture are measured using on-board equipment on the combine harvester.

Grain weight is then normalized to moisture at 15%, using the following formula:

Normalized grain weight=measured grain weight×
(100−measured moisture (as a percentage))/85
(which is 100−normalized moisture at 15%).

As an example, if the measured grain moisture is 25%, the normalized grain weight will be: normalized grain weight=measured grain weight×75/85. Yield is then expressed in a conventional unit (such as quintal per hectare).

B—Experimental Design:

Field trials were conducted in 2010 (1 location) and 2011 (1 location) In 2010, plants were sown between April 15 (for the unstressed condition) and June 02 (for stressed conditions), In 2011, plants were sown on April 28 (no stress condition) and on June 03 (stressed condition).

The experimental block comprised of 5 replicates. The experimental design was Randomized complete block or Lattice. Each replicate comprised of 10 m$^2$ plot seeded at 360 seeds/m$^2$.

Two controls were used present in this experiment as described above (a bulk null segregant T00260 and a control equivalent (NB1 line).

Results are represented in FIG. 3 with the yield expressed in (Qx/ha). This figure demonstrates that the transgenic plants present an increased yield stability (normalized for moisture). No other phenotypes were observed for these plants.

The invention claimed is:

1. A method for increasing plant yield under heat stressed conditions, the method comprising the steps of:
sowing plant seeds, wherein said plant seeds contain an expression cassette comprising a nucleic acid molecule comprising a promoter as set forth in SEQ ID NO:1 (BETL9 promoter), operatively linked to a nucleic acid coding for a protein as set forth in SEQ ID NO:2 (MRP1 protein); and
growing plants from these sowed seeds;
wherein the yield obtained from said grown plants is increased as compared to the yield obtained from plants grown from seeds which do not contain the expression cassette,
the heat stressed conditions are conditions that induce a yield decrease of at least 10% as compared to plants in non-heat stressed conditions, and
said plant is wheat.

2. A method for selecting a plant with improved yield under heat stressed conditions, the method comprising the step of:
selecting, in a population of plants, plants containing an expression cassette comprising a nucleic acid molecule comprising a promoter as set forth in SEQ ID NO:1 (BETL9 promoter), operatively linked to a nucleic acid coding for a protein as set forth in SEQ ID NO:2 (MRP1 protein);
wherein the yield obtained from plants containing the expression cassette is increased as compared to the yield obtained from plants which do not contain the expression cassette,
the heat stressed conditions are conditions that induce a yield decrease of at least 10% as compared to plants in non-heat stressed conditions, and
said plant is wheat.

3. A method for identifying a plant with improved yield under heat stressed conditions, the method comprising the step of:
identifying, in a population of plants, plants containing an expression cassette comprising a nucleic acid molecule comprising a promoter as set forth in SEQ ID NO:1 (BETL9 promoter), operatively linked to a nucleic acid coding for a protein as set forth in SEQ ID NO:2 (MRP1 protein);

wherein the yield obtained from plants containing the expression cassette is increased as compared to the yield obtained from plants which do not contain the expression cassette, the heat stressed conditions are conditions that induce a yield decrease of at least 10% as compared to plants in non-heat stressed conditions, and said plant is wheat.

* * * * *

SEQUENCE LISTING

```
<160> NUMBER OF SEQ ID NOS: 6

<210> SEQ ID NO 1
<211> LENGTH: 1911
<212> TYPE: DNA
<213> ORGANISM: Zea mays

<400> SEQUENCE: 1
ctcgagttac tcatgatggt catctaggat catagaccat ccccacagac caacatgagt      60
cttttctacg cactttgttc actcgtgtgc atcaaagaaa acttcttggt tggtcactca     120
tccaaaaatt gctctgagcc aagcatgctt atcttagagg ttttttttgag ataagcttct    180 gaaaaagaag gtgcaccttg tttgtatgag tattatacca ttcctattaa gccttggaca     240
aagatatcac aatccaccta ggccaagata tcacatttcc caacttagtc tataaaagga     300
ctagacaaga catctcctta gaagagaagc cctacctctt gtgcccataa caggcacctc     360
caacttgaga actaatttca caaagagtca cgctcttggg aactccatgt actcatatgt     420
acacactaca tctaatgcat agaaacacca agatcacatt gtactagcaa aatgtcatag     480
aagactagtt aaaaccttgt ttggtctgct caaacttaac aaatcaccta ggagacatgc     540
tagaagtatc tcaacagaga atgacaccat atagtagtgg caccaagtgc ctaatctgca     600
cacaaaaaaa tcgtaccata catgacatca aggcttaata atagagtgta tgttaaagcg     660
agcatgcaac ctatgagtgg tatgtaggag ttaggtttaa acaaggtaat ggctcaagca     720
ccacacatcc taccacaatg tcgtaataaa tataaaagca ctagcaatct atttagcatg    780
cctaaatggg atactatgag gttgggtggg atgtggcacc tttgtataat ggcccagttc     840
cttagtgtag tcttgatcct ccccgttatg ttgagactcc tctagggatt ttgtaggaat     900
catcaaattt tcataagcaa tttcttgtgc acaaagaacc aaatagattg aaaaagtttc     960
aaattcactc aaacacaaaa ccatggcaca tagcttatgt gacaaaatat ttgggacact    1020
agtttcatat tttttgagat catataagtt tattatcaaa ctcccaagga ttaaattatt    1080
ttttgaaaaa aagaaaaaa gggaaaacat cataaggtga cacatggcaa cctctgaatg    1140
```

-continued

```
actagactttt taccatctct caggtgggtc tggtcaacaa tcactgttgg tcggtcctta    1200
ccttgcctag acgggtcctt agtaggccta ctgggttgag ttatgggata aattgtggcc    1260
tagaaacata ccagtccacc aaccttggga ccacttaaaa aattgcatct ttcaccatta    1320
tactatttag atgttttttaa aaacaatca taacttttac atcgaaatca aaactagaca    1380
aattttatac tttcacagag cagcagaaat ttatacaata tgattgaata caagatgtag    1440
gacccaatgg agagaatttt ttgtctccta tatgcttgaa tacccaacat aatatcttcg    1500
caacatacta tctatctaat agaaaaatta taatatagtt aaatacttaa gtagtatcta    1560
gtggatagaa ttcaatatct cctacatgca tgaggagtaa tatctactag acatgcaaca    1620
tatttttatc tatctaatag aatatatata ataaagttaa atattatatg catcacctac    1680
tatatataat ttgatatctt ttagatgtat aagggactaa gaataatatc tctagcacac    1740
atgcaatgca ttatctatct aaatatatta tataatagtt aaatattaat tatacgtagt    1800
ctaaacctac atataagcct acccatcccc acttaaagat ctcagtgtca cacatagacc    1860
atacatctca cttcgccaaa aaaattccgt caacagttga agttataccc t              1911
```

<210> SEQ ID NO 2
<211> LENGTH: 242
<212> TYPE: PRT
<213> ORGANISM: Zea mays

<400> SEQUENCE: 2

```
Met Asn Pro Asn Phe Asn Ser Val Trp Ser Ala Pro Glu Ile Asn Met
 1               5                  10                  15

Met Asn Ser Leu Ile Thr Ser His Ile Ala Asn Asn Thr Tyr Thr Asn
             20                  25                  30

Asn Asn Gln His Val Val Ala Ser Arg Ser Ala Ile Val Asn His Asn
         35                  40                  45

Asn Phe Gly Met Pro Thr Glu Val Val Pro Val Asp Asn Met Asp
     50                  55                  60

Met Met Gln Gly Tyr Leu Met Ala Asp Thr Asp Ala Met Arg Leu Val
 65                  70                  75                  80

Gln Gly Gln Gln His Met Pro Asn Val Val Pro Asn Gln Arg Arg His
                 85                  90                  95

Ala Val Lys Phe Trp Thr Thr Asp Glu His Arg Asn Phe Leu Arg Gly
            100                 105                 110

Leu Glu Val Phe Gly Arg Gly Lys Trp Lys Asn Ile Ser Lys Tyr Phe
        115                 120                 125

Val Pro Thr Arg Thr Pro Val Gln Ile Ser Ser His Ala Gln Lys Tyr
    130                 135                 140

Phe Arg Arg Gln Glu Cys Thr Thr Glu Lys Gln Arg Phe Ser Ile Asn
145                 150                 155                 160

Asp Val Gly Leu Tyr Asp Thr Gln Pro Trp Val Arg Gln Asn Asn Ser
                165                 170                 175

Ser Ser Ser Trp Glu Ala Leu Thr Phe Thr Ala Gly Arg Ala Tyr Asn
            180                 185                 190

Asn Thr Asn Tyr Cys Ala Phe Asn Ser Leu Pro Tyr Ala Ser Ser Gln
        195                 200                 205

Ala Ser Asn Asn Gln Val Ala Thr Trp Ile Thr Asp Gln Gln Ala Thr
    210                 215                 220

Ala Ser Ser Ser Ile Ala Pro Pro Ala Thr Glu Glu Ser Gln Ile Tyr
225                 230                 235                 240
```

Asn Arg

<210> SEQ ID NO 3
<211> LENGTH: 42
<212> TYPE: DNA
<213> ORGANISM: Artificial
<220> FEATURE:
<223> OTHER INFORMATION: primer

<400> SEQUENCE: 3
aggtcgacgg gatccatgaa tcccaacttc aacagtgtgt gg                    42

<210> SEQ ID NO 4
<211> LENGTH: 34
<212> TYPE: DNA
<213> ORGANISM: Artificial
<220> FEATURE:
<223> OTHER INFORMATION: primer

<400> SEQUENCE: 4
tcaagcttat cggttatata tctggctctc ctcc                             34

<210> SEQ ID NO 5
<211> LENGTH: 30
<212> TYPE: DNA
<213> ORGANISM: Artificial
<220> FEATURE:
<223> OTHER INFORMATION: primer pBETL9forXho

<400> SEQUENCE: 5
ccctcgagtt actcatgatg gtcatctagg                                  30

<210> SEQ ID NO 6
<211> LENGTH: 32
<212> TYPE: DNA
<213> ORGANISM: Artificial
<220> FEATURE:
<223> OTHER INFORMATION: primer pBETL9revXba

<400> SEQUENCE: 6
gctctagagg gtataacttc aactgttgac gg                               32